(12) United States Patent
Schaub et al.

(10) Patent No.: US 8,410,192 B2
(45) Date of Patent: Apr. 2, 2013

(54) COMPOSITIONS BASED ON SILANE-TERMINATED POLYETHERS AND THEIR USE

(75) Inventors: Matthias Schaub, Freigericht (DE); Markus Klein, Neuss (DE); Holger Urbas, Krefeld (DE); Gottfried Knispel, Leverkusen (DE)

(73) Assignee: Heraeus Kulzer GmbH, Hanau (DE)

( * ) Notice: Subject to any disclaimer, the term of this patent is extended or adjusted under 35 U.S.C. 154(b) by 146 days.

(21) Appl. No.: 11/195,212

(22) Filed: Aug. 2, 2005

(65) Prior Publication Data

US 2006/0047063 A1    Mar. 2, 2006

(30) Foreign Application Priority Data

Aug. 19, 2004 (DE) .......... 10 2004 040 386

(51) Int. Cl.
*A61K 6/10* (2006.01)
*A61C 9/00* (2006.01)
*C08G 77/00* (2006.01)
*C08G 77/18* (2006.01)

(52) U.S. Cl. .......... 523/115; 523/109; 433/48; 433/214; 528/10; 528/38

(58) Field of Classification Search .................. 523/109, 523/113, 115; 528/28, 10, 38; 433/48, 214
See application file for complete search history.

(56) References Cited

U.S. PATENT DOCUMENTS

| | | | | |
|---|---|---|---|---|
| 4,687,533 A * | 8/1987 | Rizk et al. | .................. | 156/307.3 |
| 5,118,290 A * | 6/1992 | Muller et al. | .................... | 433/48 |
| 6,503,994 B1 * | 1/2003 | Nehren et al. | .................. | 528/17 |
| 6,749,943 B1 * | 6/2004 | Tangen et al. | .................. | 428/447 |
| 6,794,527 B1 * | 9/2004 | Wolter et al. | ................. | 556/419 |
| 6,835,760 B2 * | 12/2004 | Schaub et al. | ................ | 523/109 |
| 2002/0156149 A1 * | 10/2002 | Schaub et al. | ................ | 523/109 |
| 2003/0083399 A1 * | 5/2003 | Schaub et al. | ................ | 523/115 |
| 2004/0132949 A1 * | 7/2004 | Roesler et al. | .................. | 528/28 |
| 2004/0146713 A1 * | 7/2004 | Schaub et al. | ............ | 428/411.1 |
| 2004/0204539 A1 * | 10/2004 | Schindler et al. | ............. | 524/588 |
| 2005/0215701 A1 * | 9/2005 | Porsch et al. | .................. | 524/589 |
| 2005/0250871 A1 * | 11/2005 | Bublewitz et al. | ............ | 523/109 |

FOREIGN PATENT DOCUMENTS

| | | |
|---|---|---|
| DE | 36 36 974 A1 | 5/1988 |
| DE | 43 07 024 A1 | 9/1994 |
| DE | 44 39 769 A1 | 5/1996 |
| DE | 198 08 557 | 9/1999 |
| DE | 199 42 467 A1 | 4/2001 |
| DE | 101 04 079 A1 | 8/2002 |
| DE | 102 37 271 A1 | 3/2004 |
| DE | 102 44 693 A1 | 4/2004 |
| EP | 0 269 819 A2 | 6/1988 |
| EP | 0 939 107 A2 | 9/1999 |
| EP | 1 081 191 A2 | 3/2001 |
| EP | 1 226 808 A2 | 7/2002 |
| EP | 1 402 873 A1 | 3/2004 |
| JP | 63-112614 A | 5/1988 |
| JP | 2001-106915 A | 4/2001 |
| JP | 2002-226317 A | 8/2002 |
| JP | 2003-268229 A | 9/2003 |
| WO | WO 2004/022618 A1 | 3/2004 |
| WO | WO 2005-077321 A1 | 8/2005 |

* cited by examiner

*Primary Examiner* — Michael Pepitone
(74) *Attorney, Agent, or Firm* — Norris McLaughlin & Marcus, P.A.

(57) ABSTRACT

Compositions containing
(A) at least one silane-terminated polyether derivative with
  a content of polyether groups from 10 to 98% and
  a content of 1 to 25% terminal groups with the structure $$-NR^1-X-Si(OR^2)_m R^3_{(3-m)} \quad (I)$$

in which
m denotes 1, 2 or 3
$R^1$, $R^2$, $R^3$ independently of each other denote H or a saturated or unsaturated, linear, branched, cyclic or polycyclic hydrocarbon group with 0 to 10 heteroatoms from the group O, N, S and a total of 1 to 30 carbon atoms,
X denotes a group with the empirical formula $C_n H_{2n}$,
n denotes a whole number $\geq 3$,
with the stipulation that n>3, if $R^1$ stands for H,
(B1) water and
(B2) at least one organic or inorganic acid,
as well as optional diluents and/or fillers and/or ordinary additives,
are suitable for preparation of molding compounds, especially in the dental field.

26 Claims, No Drawings

COMPOSITIONS BASED ON SILANE-TERMINATED POLYETHERS AND THEIR USE

The invention concerns compositions based on silane-terminated polyether derivatives and their use for production of molding compounds that are used especially in dentistry.

The production of silane-terminated polyether and polyether derivatives and their use to produce molding compounds is known per se. EP 0 269 819 B1 describes the use of mixtures containing polyaddition products containing ether, urethane and urea groups with alkoxysilane terminal groups to produce molding or doubling materials in the dental field.

Similar systems are disclosed in DE 43 07 024 and DE 44 39 769, namely plastics with at least one polyaddition product containing silane, ether and urethane groups and optionally urea groups with a mostly linear molecular structure and mostly aliphatically or cycloaliphatically bonded ethers or urethane segments and a weight-average molecular weight in the range from 800 to 20,000 with a content of terminal silyl groups in which at least one ether group is present in at least one of the substituents on the silicon atom.

Mixtures based on alkoxy silyl-functional polyethers with linear or branched main chain as molding and doubling materials in dentistry are finally described in DE 101 04 079.2-42.

Two-component preparations based on silane-functionalized polyether derivatives that contain antacid components in the base component are described in DE 102 44 693.

Moreover, silane-functionalized polyether derivatives are also known as additives for activated components of condensation-crosslinking silicone compounds. Such systems are described in DE 198 08 557.

Molding compounds based on silane-terminated polyethers generally consist of a catalyst component containing water and organic and/or inorganic acids and the base component. The compounds are stored separately and mixed before use.

During use as a dental molding material the mixed preparation is introduced in the flowable state in the mouth of the patient and pressed onto the row of teeth. The molding compound then hardens within a few minutes to an elastic product.

A variety of requirements exist with respect to properties of a molding compound in the flowable and elastic state.

Important requirements exist with respect to mixability of the individual components, setting behavior of the mixed molding compound, as well as detail reproduction, dimensional accuracy and mechanical properties of the elastomeric molding compound.

The consistency of the individual components must be configured so that uniform mixing to a homogeneous mass is possible within a few seconds. This can occur, for example, in so-called tube materials by mixing by hand. In products packed in double-chamber cartridges or tubular bags, the two components are delivered through discharge devices and mixed homogeneously with static or dynamic mixers.

The material must remain in the flowable state long enough to take an impression, generally about 30 seconds to 4 minutes. After about 2 to 5 minutes residence time in the mouth the product should be converted to an elastomeric state so that removal from the mouth without adversely affecting the impression is possible. The following requirements are imposed on the set material according to EN ISO 4823:

Recovery after deformation must be at least 96.5%, detail reproduction must be at least 20 μm and the dimensional change a maximum of 1.5%.

In addition, sufficient tensile strength and elongation at break of the elastic solid are required.

In the molding compounds based on silane-terminated polyether derivatives according to the prior art, it proved to be very difficult to obtain tensile strength and hard products, which are easily mixable and have high elongation at break, in the stipulated processing time.

By increasing the average molecular weight of the employed silane-terminated polyethers, an increase in elongation at break can be achieved within certain limits. However, both the silane-terminated polyether derivatives required for this and the molding compounds obtained from them have very high viscosity. Homogeneous mixing of the compounds can only be achieved with extreme difficulty because of this high viscosity.

Molding compounds that still have acceptable mixability are characterized by viscosities (23° C., 3 s$^{-1}$) of <700 Pas.

Corresponding appropriate silane-terminated polyether derivatives from which such readily mixable compounds can be obtained are characterized by viscosities (23° C., 3 s$^{-1}$) of <160 Pas. Ordinarily, silane-terminated polyether derivatives with lower viscosities also lead to molding compounds with lower viscosities, which are then more easily mixed.

The task of the present invention is therefore to provide silane-terminated polyether derivatives, based on which preparations can be obtained that have tensile strength values of more than 1 N/mm$^2$ (determined according to DIN 53504) and a Shore A hardness from 25 to 80 (determined according to DIN 53505) after curing at a processing time of 60 to 240 s and are characterized by easy mixability and the lowest possible viscosity of the individual components, as well as high elongation at break (determined according to DIN 53504) of the set material.

This task is solved by using silane-terminated polyether derivatives having the following structural features:
a content of polyether groups from 10 to 98, preferably 50 to 90% and
a content of 1 to 25% terminal groups with the structure $$-NR^1-X-Si(OR^2)_m R^3_{(3-m)} \qquad (I)$$

in which:
R$^1$, R$^2$, R$^3$ independently of each other denote H or a saturated or unsaturated, linear, branched, cyclic or polycyclic hydrocarbon group with 0 to 10 heteroatoms from the group O, N, S and a total of 1 to 30 carbon atoms;
m denotes 1, 2 or 3;
X denotes a group with the empirical formula C$_n$H$_{2n}$;
n denotes a whole number $\geq 3$,
with the stipulation that n>3, if R$^1$ stands for H.

The structural features are then present in the same molecule or macromolecule. R$^1$, R$^2$, R$^3$, in particular, independently of each other denote H,
C$_{1-30}$ alkyl, C$_{2-20}$ alkenyl or C$_{2-20}$ alkynyl, optionally interrupted by —O—, —S— or —N<,
C$_{1-12}$ cycloalkyl, C$_{1-10}$ aryl or C$_{1-9}$ heteroaryl optionally substituted with C$_{1-6}$ alkyl, C$_{2-6}$ alkenyl or C$_{1-6}$ alkoxy or —C$_{7-12}$ aralkyl or C$_{7-12}$ alkaryl.

The invention therefore concerns compositions containing at least one of these described silane-terminated polyether derivatives as well as water and at least one organic or inorganic acid.

Preferably group X denotes a linear or branched group with the empirical formula C$_n$H$_{2n}$ with n>3,
and at least one tertiary and/or at least one quaternary C atom.

For the alkyl groups R$^1$, R$^2$, R$^3$ all straight-chain and branched groups with 1 to 30 carbon atoms are considered, like methyl, ethyl, propyl, isopropyl, butyl, sec-butyl, tertbutyl, isobutyl, pentyl, isopentyl, neopentyl, hexyl, isohexyl, heptyl, octyl, 2-ethylhexyl, nonyl, decyl, undecyl, dodecyl, octadecyl, eicosyl, quatradecyl, tridecyl, 1-methylbutyl, 2-methylbutyl, 3-methylbutyl, 2,2-dimethylpropyl, 1-ethylpropyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylbutyl, 1,2,2-trimethylbutyl, 1-ethyl-1-methylpropyl, 1-ethyl-2-methylpropyl, tridecyl, tetradecyl, pentadecyl, hexadecyl, heptadecyl, nonadecyl. Preferred groups for $R^1$ are those with 1 to 15 carbon atoms and for $R^2$ and $R^3$ those with 1 to 10 carbon atoms.

The following are considered as $C_{2-20}$ alkenyl: vinyl, allyl (propenyl), isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl, 2-octenyl, decenyl, oleyl, elaidyl, ricinoleyl, linoleyl, linolenyl, gadoleyl, arachidyl or erucyl.

The following are considered as $C_{3-20}$ alkynyl: propynyl, 3-butynyl, 2-butynyl, n-2-octynyl and n-2-octadecynyl. The $C_{2-5}$ alkenyl and $C_{3-4}$ alkynyl groups are preferred among them.

Cyclepentyl, cyclohexyl, cyclooctyl, cyclododecyl are meant as cycloalkyl groups.

Straight-chain or branched groups with 1 to 6 carbon atoms, like methoxy, ethoxy, propoxy, isopropoxy, butoxy, isobutoxy, sec-butoxy, tert-butoxy are considered for the alkoxy groups. Alkoxy groups with 1 to 4 carbon atoms are preferred.

Phenyl, 1-naphthyl or 2-naphthyl are meant by aryl groups.

The aralkyl groups with 7 to 12 carbon atoms can be benzyl, phenethyl, 2-phenethyl, 3-phenylpropyl, 1-naphthylmethyl.

Toluyl or mesityl are considered as alkaryl groups.

As alkylene groups X, straight-chain or branched, saturated alkylene groups are considered, for example: ethylethylene, tetramethylene, pentamethylene, 1-methyl-tetramethylene, 1-methyltrimethylene, 1,1-trimethylene-ethylene, 1,1-tetramethylenemethylene, n-propylene, 1-methylethylene, n-butylene, 1-methylpropylene, 2-methylenepropylene, 1,1-dimethylethylene, n-pentylene, 1-methylbutylene, 2-methylbutylene, 3-methylbutylene, 2,2-dimethylpropylene, 1-ethylpropylene, n-hexylene, 1,1-dimethylpropylene, 1,2-dimethylpropylene, 1-methylpentylene, 2-methylpentylene, 3-methylpentylene, 4-methylpentylene, 1,1-dimethylbutylene, 1,2-dimethylbutylene, 1,3-dimethylbutylene, 2,2-dimethylbutylene, 2,3-dimethylbutylene, 3,3-dimethylbutylene, 1-ethylbutylene, 2-ethylbutylene, 1,1,2-trimethylpropylene, 1,2,2-trimethylpropylene, 1-ethyl-1-methylpropylene, 1-ethyl-2-methylpropylene, n-heptylene, n-octylene, n-nonylene, n-decylene, n-undecylene, n-dodecylene, hexadecylene or octadecylene.

Preparation of the silane-terminated polyether derivatives preferably occurs in similar fashion to the method described in EP 0 269 819 B1 by conversion of OH-functional polyethers with two or more OH functions with aliphatic and/or cycloaliphatic diisocyanate, in which additional OH functional compounds, like alcohols, polyester polyols, polyolefin polyols, polycarbonate polyols or OH-terminated polysiloxanes can optionally be added and the obtained isocyanate-functional polyether derivatives are then converted with appropriate aminoalkylalkoxysilanes and optionally aliphatic and/or cycloaliphatic diamines with primary and/or secondary amino groups.

Preparation of the polyether derivatives used according to the invention can also occur by conversion of OH-functional polyether with two or more OH functions with isocyanatoalkylalkoxysilanes.

The OH-functional polyethers used to prepare the silane-terminated polyether derivatives used according to the invention are homo- or copolymerization products of epoxides, like ethylene oxide, propylene oxide, butylene oxide, tetrahydrofuran, styrene oxide or epichlorohydrin, with OH functionalities from 2 to 10, preferably 2 to 6, and a number-average molecular weight from 800 to 20,000, as described frequently in the literature.

Appropriate diisocyanates are those with aliphatically and/or cycloaliphatically bonded isocyanate groups with the formula $Q(NCO)_2$, in which Q stands for an aliphatic hydrocarbon group with 2 to 12 carbon atoms or a cycloaliphatic or mixed aliphatic-cycloaliphatic hydrocarbon group with 4 to 14 carbon atoms.

Examples of such diisocyanates are ethylene diisocyanate, tetramethylene diisocyanate, hexamethylene diisocyanate, dodecamethylene diisocyanate, cyclobutane-1,3-diisocyanate, cyclohexane-1,3- and 1,4-diisocyanate or 1-isocyanato-3,3,5-trimethyl-5-isocyanatomethylcyclohexane or any mixtures of such diisocyanates. Cycloaliphatic or mixed aliphatic-cycloaliphatic diisocyanates are preferably used to produce the polyether derivative used according to the invention. 1-Isocyanato-3,3,5-trimethyl-5-isocyanatomethylcyclohexane (isophorone diisocyanate) is particularly preferred.

Appropriate isocyanatoalkylalkoxysilanes are characterized by the following structure:

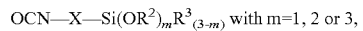

OCN—X—Si(OR$^2$)$_m$R$^3_{(3-m)}$ with m=1, 2 or 3, appropriate aminoalkylalkoxysilanes are characterized by the following structure:

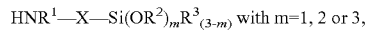

HNR$^1$—X—Si(OR$^2$)$_m$R$^3_{(3-m)}$ with m=1, 2 or 3, in which $R^1$, $R^2$, $R^3$ independently of each other denote H or a saturated or unsaturated, linear, branched, cyclic or polycyclic hydrocarbon group with 0 to 10 heteroatoms from the group O, N, S and a total of 1 to 30 carbon atoms, X denotes a group with the empirical formula $C_nH_{2n}$ with $n \geq 3$, preferably $3 \leq n \leq 20$ with the stipulation that n>3, if $R^1$=H.

Preferably $R^1$ denotes H or a hydrocarbon group with 1 to 15 carbon atoms, like methyl, ethyl, n-propyl, isopropyl, n-butyl, n-pentyl, n-ocytl, 2-ethylhexyl, phenyl, benzyl and $R^2$ and $R^3$ denote hydrocarbon groups with 1 to 10 carbon atoms, for example methyl, ethyl, n-propyl, isopropyl, n-butyl. In a special variant $R^2$ can denote a group from oxyalkyl groups, as in —CH$_2$CH$_2$—O—CH$_3$, —CH$_2$CH$_2$—O—CH$_2$CH$_2$—O—CH$_3$ or in —CH$_2$CHCH$_3$—O—CH$_2$CHCH$_3$—O—CH$_3$.

Examples are aminoalkyltrialkoxysilanes, like 4-aminobutyltrimethoxysilane, N-alkylaminopropylalkoxysilane, like N-methylaminopropyltrimethoxysilane, N-methylaminopropyltriethoxysilane, N-methylaminopropylmethyldimethoxysilane or N-ethylaminopropyltrimethoxysilane, 4-amino-3,3-dimethylbutyltrimethoxysilane, N-ethyl-aminoisobutyltrimethoxysilane, N-phenylaminopropyltrimethoxysilane, N-cyclohexylaminopropyltrimethoxysilane, N-methylaminopropyl-tris(methoxyethoxyethoxy)silane, 4-aminobutyl-tris(methoxyethyoxyethoxy)silane.

Appropriate diamines for production of the polyether derivatives used according to the invention are aliphatic cycloaliphatic or mixed aliphatic-cycloaliphatic diamines having primary or secondary amino groups with a molecular weight of 60 to 5000. Examples are ethylenediamine, tetramethylenediamine, hexamethylenediamine, 4,4'-diaminodicyclohexylmethane, 1,4-diaminocyclohexane, 4,4'-diamino-3,3'-dimethyldicyclohexylmethane, 1-amino-3,3,5-trimethyl-5-aminomethylcyclohexane or polypropylene oxide diamines.

Preparation of the silane-terminated polyether derivatives used according to the invention can occur without using tin-containing catalysts, especially organotin compounds.

Compositions (or mixtures) according to the invention obtained based on the described silane-terminated polyether derivatives generally consist of:
(A) 2 to 85%, preferably 15 to 40% silane-terminated polyether derivative with terminal groups with a structure $NR^1—X—Si(OR^2)_m R^3_{(3-m)}$ with the aforementioned meanings for $R^1$, $R^2$, $R^3$, X and m,
(B) mixtures of water with organic and/or inorganic acid,
(C) 5 to 70%, preferably 15 to 50% diluent,
(D) 10 to 90%, preferably 20 to 70% filler,
(E) 0 to 10%, preferably 0 to 8% additives like dyes, pigments, flavorings, stabilizers, inhibitors, emulsifiers.

Low-molecular compounds or polymers liquid at room temperature are considered as component (C).

Examples include glycerol, phthalic acid esters, citric acid esters, aromatic hydrocarbons, like dibenzyltoluene, aromatic and aliphatic sulfonic acid esters or polyethers liquid at room temperature, for example those used to produce component (A) or mixtures thereof. Use of aromatic hydrocarbons and polyethers is then preferred.

Inorganic fillers with an uncharged or charged surface are used as component (D), like quartz or cristobalite flour, precipitated or pyrogenic silicas. Organic fillers, like hydrogenated castor oils or castor oil derivatives, polyamides, polyesters, paraffins, waxes, fats can also be used.

Mixtures of water with organic acids or with inorganic acids can be used as component (B). The rate of the setting reaction depends on the acid strength of the employed acid. Hydrochloric acid, phosphoric acid, hexafluorophosphoric acid, hexafluoroantimonic acid, tetrafluoroboric acid, 4-toluenesulfonic acid, benzenesulfonic acid, 4-bromobenzenesulfonic acid, 4-chlorobenzenesulfonic acid, alkanesulfonic acids, carboxylic acids, like acetic acid, propionic acid, succinic acid, tartaric acid, trimellitic acid, benzoic acid, phenylacetic acid, citric acid, maleic acid, adipic acid are useable.

Mixtures of water with organic and/or inorganic acids with a weight ratio of 1:0.01 to 1:40 are preferably used.

Sulfonic acids are preferred as acids, with particular preference toluenesulfonic acid, in which the mixture with water preferably contains between 5 and 50% 4-toluenesulfonic acid.

The compositions according to the invention contain according to component (E) 0-10% additional additives, like dyes, pigments, flavorings, thixotropic agents, stabilizers, like silanes and antacids, like amines or aminosilanes, emulsifiers or other ordinary additives.

The described mixtures are generally formulated as two-component materials consisting of a base component and a catalyst component in which the base component contains component (A) and optionally component (C), (D) and (E) and the catalyst component contains component (B) and optionally component (C), (D) and (E). The basic catalyst components are then adjusted in the usual manner so that a mixture occurs in a volume ratio based to catalyst component of 1:1 to 1:10.

The compositions according to the invention are ordinarily for molding, preferably for dental medical or dental technical purposes. One-time, one-phase or multiphase dental impression taking and bite recording are particularly preferred.

The object of the invention also includes containers and mixing devices containing compounds produced from the composition according to the invention, for example, cartridges, tubes, static and dynamic mixers or mixing devices.

The invention is further explained by means of the following examples without restricting it to them. Percentages, unless otherwise stated, refer to weight, as in the rest of the description.

EXAMPLES

Synthesis of Linear Silane-Terminated Polyether Derivatives with an Average Molecular Weight of about 4000

SPEA1

700 g (0.233 mol) of a linear polypropylene oxide diol with an average molecular weight of about 3000 is dehydrated for 30 minutes at 120° C. at 5 mbar. 103.5 g (0.466 mol) isophorone diisocyanate (subsequently called IPDI) is then added and agitated under nitrogen for 4 hours at 120 to 140° C. The isocyanate content of the prepolymer is determined at 2.25%. 95.25 g (0.43 mol) N-ethylaminoisobutyltrimethoxysilane is added to the prepolymer at 30° C. under agitation and a nitrogen atmosphere. After further agitation for 60 minutes at 60° C. a clear, colorless product is obtained after cooling with a viscosity of 30 Pas at 23° C.

SPEA2

700 g (0.233 mol) of a linear polypropylene oxide diol with an average molecular weight of about 3000 is dehydrated for 30 minutes at 120° C. at 5 mbar. 103.5 g (0.466 mol) IPDI is then added and agitated under nitrogen for 4 hours at 120 to 140° C. The isocyanate content of the prepolymer is determined at 2.15%.

88.5 g (0.4 mol) 4-amino-3,3-dimethylbutyltrimethoxysilane is added to the prepolymer at 30° C. under agitation and nitrogen. After further agitation for 60 minutes at 60° C. a clear, colorless product with a viscosity of 133 Pas at 23° C. is obtained after cooling.

SPEA3

Comparative Example 700 g (0.233 mol) of a linear polypropylene oxide diol with an average molecular weight of about 3000 is dehydrated for 30 minutes at 120° C. at 5 mbar. 103.5 g (0.466 mol) IPDI is then added and agitated under nitrogen at 120 to 140° C. for 4 hours. The isocyanate content of the prepolymer is determined at 2.20%.

90.7 g (0.41 mol) aminopropyltriethoxysilane is added to the prepolymer at 30° C. under agitation and nitrogen. After further agitation for 60 minutes at 60° C. a clear, colorless product with a viscosity of 105 Pas at 23° C. is obtained after cooling.

Synthesis of Linear Silane-Terminated Polyether Derivatives with an Average Molecular Weight of 5500.

SPEB1

700 g (0.233 mol) of a linear polypropylene oxide diol with an average molecular weight of about 3000 is dehydrated for 30 minutes at 120° C. at 5 mbar. 86.46 g (0.39 mol) IPDI together with 0.05 g dibutyltin dilaurate is then added and agitated under nitrogen for 3 hours at 100° C. The isocyanate content of the prepolymer is determined at 1.65%. 67.38 g (0.3 mol) N-ethylaminoisobutyltrimethoxysilane is then added under agitation and nitrogen at 30° C. to the prepolymer. After further agitation for 60 minutes at 60° C. a clear, colorless product with a viscosity of 32 Pas at 23° C. is obtained after cooling.

SPEB2

700 g (0.233 mol) of a linear polypropylene oxide diol with an average molecular weight of about 3000 is dehydrated for 30 minutes at 120° C. at 5 mbar. 86.46 g (0.39 mol) IPDI together with 0.05 g dibutyltin dilaurate is then added and agitated under nitrogen for 3 hours at 100° C. The isocyanate content of the prepolymer is determined at 1.65%. 70.6 g (0.3 mol) N-butylaminopropyltrimethoxysilane is then added to the prepolymer at 30° C. under agitation and nitrogen. After further agitation for 60 minutes at 60° C. a clear, colorless product with a viscosity of 42 Pas at 23° C. is obtained after cooling.

SPEB3

Comparative Example 700 g (0.233 mol) of a linear polypropylene oxide diol with an average molecular weight of about 3000 is dehydrated for 30 minutes at 120° C. at 5 mbar. 86.46 g (0.39 mol) IPDI together with 0.05 g dibutyltin dilaurate is then added and agitated under nitrogen for 3 hours at 100° C. The isocyanate content of the prepolymer is determined at 1.65%. 66.4 g (0.3 mol) aminopropyltriethoxysilane is then added to the prepolymer at 30° C. under agitation and nitrogen. After further agitation for 60 minutes at 60° C. a clear, colorless product with a viscosity of 116 Pas at 23° C. is obtained after cooling.

Synthesis of Linear Silane-Terminated Polyether Derivatives with an Average Molecular Weight of 7000

SPEC1

700 g (0.233 mol) of a linear polypropylene oxide diol with an average molecular weight of about 3000 is dehydrated for 30 minutes at 120° C. at 5 mbar. 77.4 g (0.35 mol) IPDI together with 0.05 g dibutyltin dilaurate is then added and agitated under nitrogen for 3 hours at 100° C. The isocyanate content of the prepolymer is determined at 1.15%. 46.5 g (0.21 mol) N-ethylaminoisobutyltrimethoxysilane is then added to the prepolymer at 30° C. under agitation and nitrogen. After further agitation for 60 minutes at 60° C. a clear, colorless product with a viscosity of 80 Pas at 23° C. is obtained after cooling.

SPEC2

Comparative Example 700 g (0.233 mol) of a linear polypropylene oxide diol with an average molecular weight of about 3000 is dehydrated for 30 minutes at 120° C. at 5 mbar. 77.4 g (0.35 mol) IPDI together with 0.05 g dibutyltin dilaurate is then added and agitated under nitrogen for 3 hours at 100° C. The isocyanate content of the prepolymer is determined at 1.15%. 46.5 g (0.21 mol) aminopropyltriethoxysilane is then added to the prepolymer at 30° C. under agitation and nitrogen. After further agitation for 60 minutes at 60° C. a clear, colorless product with a viscosity of 165 Pas at 23° C. is obtained after cooling.

TABLE 1

Properties of silane-terminated polyether derivatives used according to the invention SPEA1, SPEA2, SPEB1, SPEB2 and SPEC1 as well as the silane-terminated polyether derivatives SPEA3, SPEB3 and SPEC2 used in the comparative examples:

|  | SPEA 1 | SPEA 2 | SPEA 3 | SPEB 1 | SPEB 2 | SPEB 3 | SPEC 1 | SPEC 2 |
|---|---|---|---|---|---|---|---|---|
| Average molecular weight about | 4000 | 4000 | 4000 | 5500 | 5500 | 5500 | 7000 | 7000 |
| Content of polyether groups (%) | 78.0 | 78.5 | 78.3 | 82.0 | 81.7 | 82 | 85 | 85 |
| Content of terminal groups of the structure $NR^1$—X—$Si(OR^2)_m R^3_{(3-m)}$, in which X stands for $C_n H_{2n}$ (%) | 10.6 | 9.9 | 10.1 | 7.9 | 8.2 | 7.8 | 5.6 | 5.6 |
| n | 4 | 6 | 3 | 4 | 3 | 3 | 4 | 3 |
| $R^1$ | $C_2H_5$ | H | H | $C_2H_5$ | $C_4H_9$ | H | $C_2H_5$ | H |
| Viscosity (23° C., 3 s$^{-1}$) [Pas] | 30 | 133 | 105 | 32 | 42 | 116 | 80 | 165 |

Preparation of the Base Components:

In a laboratory dissolver the components of the base components (composition see Table 2) are mixed to a homogeneous pasty mass for 3 hours at a pressure of <50 mbar.

TABLE 2

Percentage composition and viscosities of base components BA1, BA2, BB1, B2 and BC according to the invention. Comparative examples: VBA, VBB, VBC.

|  | BA1 | BA2 | VBA | BB1 | BB2 | VBB | BC | VBC |
|---|---|---|---|---|---|---|---|---|
| SPEA1 | 20 |  |  |  |  |  |  |  |
| SPEA2 |  | 20 |  |  |  |  |  |  |
| SPEA3 |  |  | 20 |  |  |  |  |  |
| SPEB1 |  |  |  | 20 |  |  |  |  |
| SPEB2 |  |  |  |  | 20 |  |  |  |
| SPEB3 |  |  |  |  |  | 20 |  |  |

TABLE 2-continued

Percentage composition and viscosities of base components BA1, BA2, BB1, B2 and BC according to the invention. Comparative examples: VBA, VBB, VBC.

|  | BA1 | BA2 | VBA | BB1 | BB2 | VBB | BC | VBC |
|---|---|---|---|---|---|---|---|---|
| SPEC1 |  |  |  |  |  |  | 20 |  |
| SPEC2 |  |  |  |  |  |  |  | 20 |
| Dibenzyltoluene | 20 | 20 | 20 | 20 | 20 | 20 | 20 | 20 |
| Quartz flour | 56 | 56 | 56 | 56 | 56 | 56 | 56 | 56 |
| Hydrogenated castor oil | 4 | 4 | 4 | 4 | 4 | 4 | 4 | 4 |
| Viscosity ($3\ s^{-1}$, 23° C.) | 304 | 319 | 480 | 350 | 374 | 593 | 225 | 615 |

Preparation of the Catalyst Component:

Preparation of the catalyst component occurs according to DE 101 04 079 A1, example 3. The different base components are mixed with the catalyst components in a weight ratio of 5:1. On the mixtures the processing times (according to DIN EN ISO 4823), Shore A hardness (according to DIN 5305), tensile strength and elongation at break (according to DIN 53504) are determined. Compositions according to the invention each have a distinctly higher elongation at break than the corresponding comparative examples within series A, B and C.

TABLE 3

Properties of mixtures A1, A2, B1, B2 and C according to the invention; VA, VB, VC: comparative examples.

|  | Series A | | | Series B | | | Series C | |
|---|---|---|---|---|---|---|---|---|
|  | A1 | A2 | VA | B1 | B2 | VB | C | VC |
| Processing time | 1.55 | 1.75 | 2.3 | 2.0 | 2.3 | 2.2 | 2.6 | 2.8 |
| Shore A (1 h) | 50 | 62 | 64 | 54 | 50 | 58 | 50 | 55 |
| Tensile strength | 2.2 | 2.9 | 2.5 | 3.2 | 1.7 | 2.4 | 2.8 | 2.4 |
| Elongation at break [%] | 76 | 61 | 44 | 86 | 87 | 57 | 113 | 73 |

What is claimed is:

1. A composition comprising:
(A) at least one silane-terminated polyether derivative with a content of polyether groups from 10 to 98% and a content of 1 to 25% terminal groups with the structure

  (I)

in which
m denotes 1, 2 or 3
$R^1$, $R^2$, $R^3$ independently of each other denote H or a saturated or unsaturated, linear, branched, cyclic or polycyclic hydrocarbon group with 0 to 10 heteroatoms from the group O, N, S and a total of 1 to 30 carbon atoms,
X denotes a group with the empirical formula $C_nH_{2n}$,
n denotes an integer provided $3 \leq n \leq 20$,
with the proviso that if $R^1$ stands for H, then (i) n>3 and (ii) X comprises at least one tertiary and/or one quaternary carbon atom,
(B1) water, and
(B2) at least one organic or inorganic acid.

2. Composition according to claim 1, in which the hydrocarbon group $R^1$, $R^2$ or $R^3$:
denotes $C_{1-30}$ alkyl, $C_{2-20}$ alkenyl or $C_{2-20}$ alkynyl optionally interrupted by —O—, —S— or —N<,
denotes $C_{1-12}$ cycloalkyl, $C_{1-10}$ aryl, $C_{1-9}$ heteroaryl, optionally substituted with $C_{1-6}$ alkyl, $C_{2-6}$ alkenyl or $C_{1-6}$ alkoxy,
denotes $C_{7-12}$ aralkyl or $C_{7-12}$ alkaryl.

3. Composition according to claim 1, in which (B) the components B1 and B2 are present as a mixture.

4. Composition according to claim 1, wherein component (A) has a content of polyether groups from 50 to 90%.

5. Composition according to claim 1, wherein component (A) has terminal groups of the structure $NR^1$—X—Si$(OR^2)_m R^3_{(3-m)}$, with m=1, 2 or 3 in which X denotes a group with the empirical formula $C_nH_{2n}$ with n>3.

6. Composition according to claim 1, wherein component (B) comprises mixtures containing water and organic and/or inorganic acids in weight ratios of 1:0.01 to 1:40.

7. Composition according to claim 1, which further comprises:
(C) 5 to 70% diluent and/or
(D) 10 to 90% filler and/or
(E) 0 to 10% ordinary additives.

8. Composition according to claim 1, which further comprises:
(C) 15 to 50% diluent and/or
(D) 20 to 70% filler and/or
(E) 0 to 8% ordinary additives.

9. Composition according to claim 7, wherein component (E) is one or more members selected from the group consisting of dyes, pigments, flavorings, stabilizers, inhibitors, and emulsifiers.

10. A dental compound comprising a composition according to claim 1.

11. A dental molding comprising a composition according to claim 1.

12. Container comprising at least one composition according to claim 1.

13. Mixing apparatus comprising at least one composition according to claim 1.

14. A composition comprising:
(A) at least one silane-terminated polyether derivative with a content of polyether groups from 10 to 98% and a content of 1 to 25% terminal groups with the structure

  (I)

in which
m denotes 1, 2 or 3,
$R^1$ denotes an alkyl, cycloalkyl, phenyl, benzyl or carbamate group,
$R^2$ and $R^3$ independently of each other denote H or a saturated or unsaturated, linear, branched, cyclic or polycyclic hydrocarbon group with 0 to 10 heteroatoms from the group O, N, S and a total of 1 to 30 carbon atoms, X denotes a group with the empirical formula $C_nH_{2n}$, and comprises at least one tertiary and/or quaternary carbon atom, n denotes an integer $\geq 3$, (B1) water, and (B2) at least one organic or inorganic acid.

15. Composition according to claim 14, in which the hydrocarbon group $R^2$ or $R^3$:

denotes $C_{1-30}$ alkyl, $C_{2-20}$ alkenyl or $C_{2-20}$ alkynyl optionally interrupted by —O—, —S— or —N<, denotes $C_{1-12}$ cycloalkyl, $C_{1-10}$ aryl, $C_{1-9}$ heteroaryl, optionally substituted with $C_{1-6}$ alkyl, $C_{2-6}$ alkenyl or $C_{1-6}$ alkoxy, denotes $C_{7-12}$ aralkyl or $C_{7-12}$ alkaryl.

16. Composition according to claim 14, in which (B) the components B1 and B2 are present as a mixture.

17. Composition according to claim 14, wherein component (A) has a content of polyether groups from 50 to 90%.

18. Composition according to claim 14, wherein component (A) has terminal groups of the structure $NR^1$—X—Si$(OR^2)_m R^3_{(3-m)}$, with m=1, 2 or 3 in which X denotes a group with the empirical formula $C_nH_{2n}$ with n>3.

19. Composition according to claim 14, wherein component (B) comprises mixtures containing water and organic and/or inorganic acids in weight ratios of 1:0.01 to 1:40.

20. Composition according to claim 14, which further comprises:

(C) 5 to 70% diluent and/or (D) 10 to 90% filler and/or (E) 0 to 10% ordinary additives.

21. Composition according to claim 14, which further comprises:

(C) 15 to 50% diluent and/or (D) 20 to 70% filler and/or (E) 0 to 8% ordinary additives.

22. Composition according to claim 20, wherein component (E) is one or more members selected from the group consisting of dyes, pigments, flavorings, stabilizers, inhibitors, and emulsifiers.

23. A dental compound comprising a composition according to claim 14.

24. A dental molding comprising a composition according to claim 14.

25. Container comprising at least one composition according to claim 14.

26. Mixing apparatus comprising at least one composition according to claim 14.

* * * * *